United States Patent [19]

Klibanov et al.

[11] Patent Number: 4,601,987

[45] Date of Patent: Jul. 22, 1986

[54] ENZYMATIC PRODUCTION OF OPTICAL ISOMERS OF 2-HALOPROPIONIC ACIDS

[75] Inventors: Alexander M. Klibanov, Boston; Gerald Kirchner, Hyde Park, both of Mass.

[73] Assignee: Massachusetts Institute of Technology, Cambridge, Mass.

[21] Appl. No.: 706,039

[22] Filed: Feb. 27, 1985

[51] Int. Cl.[4] ............ C07P 41/00; C12P 7/40; C12P 7/52
[52] U.S. Cl. .................... 435/280; 435/136; 435/141
[58] Field of Search .............. 435/280, 141, 136

[56] References Cited

FOREIGN PATENT DOCUMENTS 0094295 6/1982 Japan ............................ 435/280
2055802A 3/1981 United Kingdom .

OTHER PUBLICATIONS

"Lipase-Catalyzed Production of Optically Active Acids via Asymmetric Hydrolysis of Esters", Cambou, B. and Klibanov, A. M., *Appl. Biochem. Biotech.*, 9, 255 (1984).
Abstract of Japanese Patent JP 57/94295 A2.
"Enzymatic Catalysis in Organic Media at 100° C.", Zaks, A. and Klipanov, M. *Science*, 224, 1249 (1984).
"Preparative Production of Optically Active Esters and Alcohols Using Esterase-Catalyzed Stero-Specific Transesterfication in Organic Media", Cambou, B. and Klibanov, A. M., *J. Am. Chem. Soc.*, 1984, 106 2687.

Primary Examiner—Sidney Marantz
Assistant Examiner—L. Krawczewicz
Attorney, Agent, or Firm—Hamilton, Brook, Smith & Reynolds

[57] ABSTRACT

A method of resolving racemic 2-halopropionic acids by lipase-catalyzed asymmetric esterification in an organic medium is disclosed.

17 Claims, 1 Drawing Figure

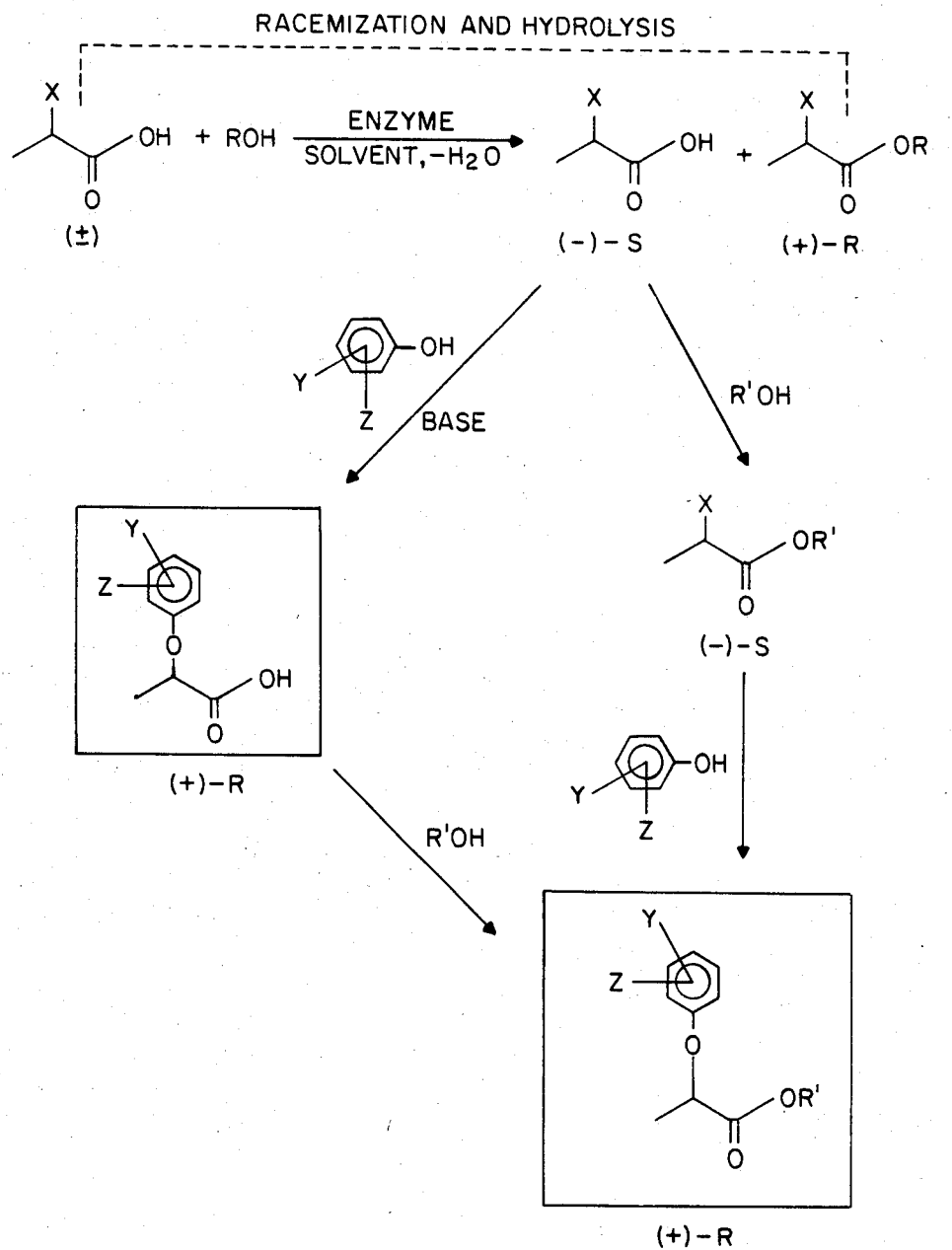

ENZYMATIC PRODUCTION OF OPTICAL ISOMERS OF 2-HALOPROPIONIC ACIDS

DESCRIPTION

1. Field of the Invention

This invention is in the field of chemistry.

2. Background of the Invention

2-Phenoxypropionic acids and their esters are widely used as herbicides. Only the R optical isomers of these compounds are biologically active. In order to increase the efficiency of the herbicides, and reduce dosage and side-effects, it is desirable to use the R isomer rather than the racemic mixture.

2-Phenoxypropionic acids are usually synthesized from 2-halo-(2-chloro- or 2-bromo-) propionic acid and phenols. If optically pure 2-halopropionic acid is used as a starting material, then optically pure 2-phenoxypropionic acid is obtained.

However, because nearly all chemical syntheses of 2-halopropionic acids afford racemic mixtures the optical isomers must be subsequently separated. Racemic mixtures of 2-halopropionic acids can be resolved either chemically or enzymatically. Chemical processes of resolution (e.g. fractional crystallization) are generally laborious, inefficient and time consuming. Enzymatic techniques developed thus far include lipase catalyzed, asymmetric hydrolysis of the esters of 2-halopropionic acids in water.

DISCLOSURE OF THE INVENTION

This invention constitutes a method of resolving racemic 2-halopropionic acids by enzyme-catalyzed asymmetric esterification in an organic medium. A stereospecific lipase is used to catalyze selectively the esterification of one optical isomer of racemic 2-halopropionic acid. This selective esterification can be carried out in an organic solvent, because stereospecific lipases can function in essentially anhydrous organic media to preferentially catalyze the esterification of one optical isomer of a racemic mixture of 2-halopropionic acids. The esterified optical isomer can then be separated readily from the unesterified optical isomer to provide either one of the optical isomers. Once separated, the esterified isomer can be used as such or hydrolyzed to yield the counterpart optical isomer of the 2-halopropionic acid.

BRIEF DESCRIPTION OF THE DRAWINGS

The FIGURE illustrates the synthesis of the (+)-R-2-phenoxypropionic acids by the method of the invention.

BEST MODE OF CARRYING OUT THE INVENTION

This invention is founded upon the discovery that stereospecific lipases can function in an anhydrous organic medium to catalyze asymmetric esterification of 2-halopropionic acids. For example, the lipase from the yeast *Candida cylindracea* preferentially catalyzes the esterification of (+)-R-2-halopropionic acid in organic solvents. Because of the activity of the enzyme in such systems, lipase-catalyzed asymmetric esterification can be employed to resolve racemic 2-halopropionic acid in an organic medium.

To resolve racemic 2-halopropionic acids by lipase-catalyzed asymmetric esterification in an organic medium, a mixture of the racemic 2-halopropionic acid, an alcohol and a stereospecific lipase is formed in an organic solvent. The 2-halopropionic acid can be 2-bromo or 2-chloropropionic acid. The alcohol used to esterify the 2-halopropionic acid can be any alcohol which reacts with 2-halopropionic acids to form an ester. Preferred alcohols are primary aliphatic alcohols such as methanol, ethanol, n-propanol and n-butanol.

The organic solvent can be selected from a variety of organic solvents. Suitable solvents are hexane, benzene, chloroform, dichloromethane, petroleum ether and toluene. The solvent can be essentially anhydrous.

The stereospecific lipase can be any lipase (EC. 3.1.1.3). The preferred lipase for selective esterification of the R isomer of 2-halopropionic acid is the lipase from the yeast *Candida cylindracea*. Porcine pancreatic lipase may also be used, but its activity and stereoselectivity is not as high as that of the lipase from *C. cylindracea* in organic media. Other lipases useful in the method are wheat germ lipase and the lipases from *Rhizopus arrhizus, Geotrichum candidum, Rhizopus delamar, Chromobacterium viscosum*, (all available from Sigma Chemical Co., St. Louis, Mo.), *Aspergillus niger, Mucor,* and *Pseudomonas* species, (available from Amano International Enzyme Company, Troy, Va.).

Commercial preparations of lipases normally contain a certain amount of water associated with the enzyme. It appears that the enzymes must be hydrated to at least some degree because completely dehydrated enzyme preparations are not active in anhydrous organic media. Consequently, the enzyme is added to the organic solvent in the hydrated state.

The esterification reaction is allowed to proceed until the desired amount of an optical isomer of the 2-halopropionic acid is converted to its ester. The objective is to maximize both the chemical and the optical yield of the desired optical isomer. When the desired product is the esterified optical isomer of the 2-halopropionic acid, the reaction should be halted when a degree of conversion of less than about 50% is obtained. When the acid is desired the degree of conversion should be greater than 50%. The degree of conversion to the ester can be monitored by conventional techniques such as gas chromatography.

The unreacted isomer of 2-halopropionic acid and the esterified isomer can be separated by any suitable technique for separating an acid from its ester, for example, by chromatography or by aqueous extraction. This yields one optical isomer of the acid. The separated ester can then be hydrolyzed to yield the corresponding optical isomer of the 2-halopropionic acid.

If the unreacted isomer is the desired product, the esterified isomer can be hydrolyzed and racemized to form a racemic mixture of the 2-halopropionic acid. The resulting racemic mixture can be resolved again. The recycling process can be repeated until virtually all of the original racemic mixture is converted to the desired isomer. A convenient method of hydrolyzing and racemizing the esterified is described below in connection with the description of the synthesis of 2-phenoxypropionic acids.

Resolution of racemic 2-halopropionic acid by lipase-catalyzed asymmetric esterification in organic media has important advantages over lipasecatalyzed asymmetric hydrolysis. First, the 2-halopropionic acids need not be converted to the ester beforehand. Thus, by selecting the appropriate lipase, a desired optical isomer can be obtained with one less synthetic step. Second, because lipases are insoluble in organic solvents, the enzymes can be easily recovered and reused when resolution is completed. Third, lipases are much more stable in organic media than in water.

2-Halopropionic acids are intermediates in the synthesis of 2-phenoxypropionic acids which are valuable herbicides. The method of this invention provides for the production of optically pure S isomer of 2-halopropionic acid which can be used to synthesize optically pure (+)-R-2-phenoxypropionic acids, the biological active isomer of the compound. The scheme in the FIGURE illustrates the synthesis of this isomeric form of the herbicide.

The substituent X is Cl or Br. ROH is the alcohol used to esterify the acid. The R radical of the alcohol is preferably a lower alkyl radical, e.g., methyl, ethyl, n-propyl, or n-butyl. The phenyl ring substituents Y and Z are meant to designate a variety of substituted phenols which may be used to produce the correspondingly substituted 2-phenoxypropionic acid. The substituents can be, for example, halogens, alkyl radicals such as methyl, ethyl, etc., hydroxyl groups and nitro groups. Examples of some substituted phenols for producing the corresponding 2-phenoxypropionic acid are 2,4-dichloro-, 4 chloro-, 2-methyl-4-chloro-, and 2,4,5-trichlorophenol.

To synthesize the R enantiomer of 2-phenoxypropionic acids the S enantiomer of the intermediate 2-halopropionic acid is required. Thus indicated in the scheme, the stereospecific lipase is one which preferentially catalyzes the esterification of only one isomer of the 2-halopropionic acid. As described above, the lipase from *Candida cylindracea* has the depicted specificity. The organic medium for the reaction can be any of the solvents listed above.

After the preferential conversion of the R isomer to its ester, the latter is then separated from the unreacted S isomer. The S isomer is then reacted with the phenol in the presence of a base to produce the 2-phenoxypropionic acid. In the reaction of the S isomer of the 2-halopropionic acid and the phenol, inversion at the chiral 2-carbon occurs to yield the R isomer of the 2-phenoxypropionic acid. If desired, the resulting R isomer of the 2-phenoxypropionic acid can then be esterified. An alternative way to produce the ester of the R isomer of 2-phenoxypropionic acid is to esterify the S-isomer of the 2-halopropionic acid, then react the esterified 2-halopropionic acid with the phenol.

As represented in the scheme, the esterified R-enantiomer of the 2-halopropionic acid can be recycled. The esterified R isomer can be hydrolyzed and racemized, and the resulting racemic mixture resolved to yield more of the S isomer. This recycling process can be repeated until essentially all of the original racemic 2-halopropionic acid is converted to the S isomer.

A convenient one-step procedure for simultaneously hydrolyzing and racemizing the esterified isomer is to subject the isomer to concentrated acid HX, where X is the same halogen atom as that of the 2-halopropionic acid. The ester is added to an aqueous solution of concentrated hydrogen halide and the solution is heated to a temperature of about 50°–100° C. and maintained at that temperature until hydrolysis is complete. The procedure yields hydrolyzed, racemic mixture of the 2-halopropionic acid.

The method is further illustrated by the following examples:

EXAMPLE 1

Resolution of 2-Chloropropionic acid

The resolution of 2-chloropropionic acid is shown in the following equation.

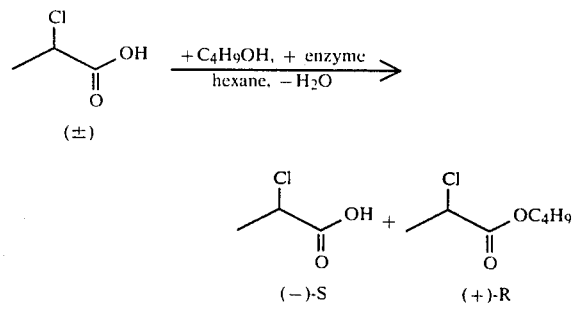

4.34 g (0.04 moles) of 2-chloropropionic acid and 11.0 ml of 1-butanol (0.12 moles) were dissolved in 400 ml of hexane and 2.0 g (5 mg/ml) of lipase from *Candida cylindracea* were added. The reaction mixture was vigorously shaken at 30° C. The degree of conversion was followed by gas chromatography (g.c.).

To isolate the ester, the reaction was stopped when 42% of the theoretical amount of the ester was formed (after 6 h). The solution was filtered, and the filtrate was washed four times with 0.5 M NaHCO$_3$ solution, followed by three washings with water. The organic phase was dried with MgSO$_4$ and evaporated in a rotary evaporator. The remainder was distilled at 10 mm Hg. At 71°–73° C. 2.4 g of butyl (+)-R-2-chloropropionate (86.8% yield) were obtained. The ester was 98.7% pure (by gas chromatography) and had specific optical rotation $[\alpha]^{23} = +7.48°$ (c=1, CHCl$_3$).

To isolate the acid, the reaction was carried out with the same amount of starting materials and was stopped when 68% of the ester was formed (after 14.5 h). After filtration, the filtrate was washed four times with 0.5 M NaHCO$_3$ solution. The aqueous phase was washed with dichloromethane and then acidified with 6N HCl to bring the pH to 1.5 and again extracted with dichloromethane (four times). The organic fractions were combined, dried with MgSO$_4$, solvent evaporated, and the remaining crude acid was distilled (bp. 81°–83° C. at 11 mm Hg). As a result, 1.33 g of (−)-S-2-chloropropionic acid (95.7% yield, 98.3% purity by g.c.) with specific optical rotation of $[\alpha]^{23} = -15.1°$ (c=1, CHCl$_3$) were obtained. Using literature data for 2-chloropropionic acid, [W. Gaffield and W. G. Galleta, Tetrahedron 27, 915 (1971)] this value represents an enantiomeric excess of 95%.

EXAMPLE 2

Resolution of 2-Bromopropionic acid

The resolution of 2-bromopropionic acid is shown in the following equation.

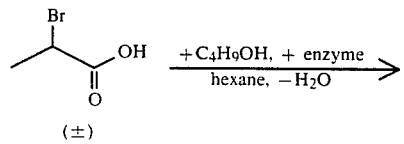

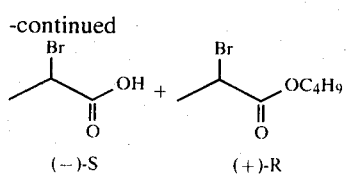

Using the same procedure employed for 2-chloropropionic acid in Example 1, the following results were obtained for 2-bromopropionic acid:

Starting from 6.1 g (0.04 moles) of 2-bromopropionic acid, 11 ml (0.12 moles) of 1-butanol and 2.0 g of lipase from *Candida cylindracea* in 400 ml hexane, the degree of conversion reached 45% after 6 h. At that point the reaction was stopped, and the ester isolated as described in Example 1.

Butyl(+)-R-2-bromopropionate: bp 84°–86° C. at 14 mm Hg yield 3.31 g (88.2%), 97.4% pure by g.c. $[\alpha]^{23} = +18.4°$ (c=1, CHCl$_3$)

With the same amount of starting materials, another reaction was started and worked up when the formation of the ester reached 78% after 14.5 h (as described for the isolation of 2-chloropropionic acid)

(−)-S-2-bromopropionic acid: bp 97°–98° C. at 11 mm Hg yield 1.29 g (96.1%), 98.7% purity by g.c. $[\alpha]^{23} = -26.4°$ (c=1, CHCl$_3$) ee=99.8%

In additional Examples, the resolution has been successfully carried out in toluene, petroleum ether, methylene chloride, chloroform and ether.

EXAMPLE 3

Racemization procedure

To recycle the butyl(+)-R-2-bromopropionate, the undesired enantiomer for the synthesis of 2-phenoxypropionic acids, the ester was simultaneously hydrolyzed and racemized as follows:

1.0 g (4.78 mmoles) of butyl(+)-R- 2-bromopropionate was added to 5 ml of HBr (48%), and the solution was stirred for 14 h at 90° C. After cooling to room temperature the reaction mixture was extracted with dichloromethane. The organic phase was dried with MgSO$_4$ and evaporated. The remainder was identified as 2-bromopropionic acid (96.5% pure by g.c.) and showed no optical rotation. Hence the above procedure afforded both hydrolysis of the R-butyl ester and racemization of the acid formed. The yield of the racemic acid was 0.68 g (93%).

INDUSTRIAL APPLICABILITY

Lipase-catalyzed, asymmetric esterification in an organic medium provides a method for resolving optical isomers of 2-halopropionic acids. The resolved isomers can be used in synthesis of optically pure products. For example, the S isomer of 2-halopropionic can be used to synthesize optically pure (+)-R-2-phenoxypropionic acids, a valuable herbicide.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of resolving racemic 2-halopropionic acids, comprising the steps of:
   (a) forming a reaction mixture of racemic 2-halopropionic acid, an alcohol and a stereospecific lipase in an organic medium under conditions whereby the lipase preferentially catalyzes esterification of only one optical isomer of the 2-halopropionic acid to yield the ester of the isomer; and
   (b) separating the esterified isomer and the unesterified isomer of the 2-halopropionic acid to obtain a first optical isomer of 2-halopropionic acid and the ester of the second optical isomer.

2. A method of claim 1, wherein the 2-halopropionic acid is 2-bromo or 2-chloropropionic acid.

3. A method of claim 1, wherein the alcohol is methanol, ethanol, n-propanol or n-butanol.

4. A method of claim 1, wherein the stereospecific lipase is a lipase from *Candida cylindracea*.

5. A method of claim 1, wherein the organic medium is hexane, benzene, chloroform, dichloromethane petroleum ether or toluene.

6. A method of claim 1, further comprising the step of hydrolyzing the esterified isomer to obtain corresponding second optical isomer of the 2-halopropionic acid.

7. A method of claim 1, further comprising the steps of:
   (c) hydrolyzing and racemizing the esterified isomer to obtain racemic 2-halopropionic acid and,
   (d) repeating steps a–c until the original racemic 2-halopropionic acid has been coverted to the first optical isomer.

8. A method of claim 7, wherein the esterified isomer is hydrolyzed and racemized by dissolving the ester in aqueous, concentrated acid HX, wherein X is the same halogen atom as that of the 2-halopropionic acid; and heating the resulting solution to a temperature of about 50°–100° C.

9. A method of producing optically pure (+)-R-2-phenoxypropionic acids comprising the steps of:
   (a) forming a reaction mixture of a racemic 2-halopropionic acid, an alcohol and a stereospecific lipase in an organic medium under conditions whereby the lipase preferentially catalyzes the esterification of (+)-R-2-halopropionic acid;
   (b) separating the unesterified (−)-S-2-halopropionic acid from the ester of (+)-R-2-halopropionic acid;
   (c) reacting the (−)-S-2-halopropionic acid with a phenol under basic conditions to yield (+)-R-2-phenoxypropionic acid.

10. A method of claim 9, for producing optically pure esters of (+)-R-2-phenoxypropionic acids, further comprising the step of:
    (d) esterifying the (+)-R-2-phenoxypropionic acid to obtain an ester of (+)-R-2-phenoxypropionic acid.

11. A method of claim 9, wherein the 2-halopropionic acid is 2-chloro- or 2-bromopropionic acid.

12. A method of claim 9, wherein the alcohol is methanol, ethanol, n-propanol or n-butanol.

13. A method of claim 9, wherein the stereospecific lipase is a lipase from *Candida cylindracea*.

14. A method of claim 9, wherein the organic medium is hexane, benzene, chloroform, dichloromethane, petroleum ether or toluene.

15. A method of claim 9, further comprising the steps of:
    (d) hydrolyzing the ester of (+)-R-2-halopropionic acid;
    (e) racemizing the resulting (+)-R-2-halopropionic acid to obtain racemic 2-halopropionic acid; and repeating steps a–e until the 2-halopropionic acid has been converted to the (+)-R-2-phenoxypropionic acid.

16. A method of claim 15, wherein the esterified isomer is hydrolyzed and racemized by dissolving the ester in aqueous, concentrated acid HX, wherein X is the same halogen atom as that of the 2-halopropionic acid; and heating the resulting solution to a temperature of about 50°–100° C.

17. A method of producing optically pure esters of (+)-R-2-phenoxypropionic acids, comprising the steps of:

(a) forming a reaction mixture of a racemic 2-halopropionic acid, an alcohol and a stereospecific lipase in an organic medium under conditions whereby the lipase preferentially catalyzes the esterification of (+)-R-2-halopropionic acids;
(b) separating the unesterified (−)-S-2-halopropionic acid from the ester of (+)-R-2halopropionic acid;
(c) esterifying the (−)-S-2-halopropionic acid to obtain an ester; and
(d) reacting the ester of (−)-S-2-halopropionic acid with a phenol under basic conditions to form an ester of (+)-R-2-phenoxypropionic acid.

* * * * *